US 6,500,991 B2

(12) United States Patent
Wiese et al.

(10) Patent No.: US 6,500,991 B2
(45) Date of Patent: Dec. 31, 2002

(54) STABILIZING RHODIUM CATALYSTS FOR THE HYDROFORMYLATION OF OLEFINS

(75) Inventors: Klaus-Diether Wiese, Haltern (DE); Martin Trocha, Essen (DE); Dirk Röettger, Recklinghausen (DE); Walter Töetsch, Marl (DE); Alfred Kaizik, Marl (DE); Wilfried Büschken, Haltern (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/960,936

(22) Filed: Sep. 25, 2001

(65) Prior Publication Data

US 2002/0065437 A1 May 30, 2002

(30) Foreign Application Priority Data

Sep. 29, 2000 (DE) .......................... 100 48 301

(51) Int. Cl.⁷ .............................................. C07C 45/50
(52) U.S. Cl. ....................... 568/454; 568/451
(58) Field of Search ................... 568/451, 454

(56) References Cited

U.S. PATENT DOCUMENTS

| 4,400,547 A | 8/1983 | Dawes et al. |
| 5,731,472 A | 3/1998 | Leung et al. |
| 5,767,321 A | 6/1998 | Billig et al. |

FOREIGN PATENT DOCUMENTS

| DE | 33 38 340 | 3/1984 |
| EP | 0 149 894 | 7/1985 |
| EP | 0 272 608 | 6/1988 |
| JP | 63-208540 | 8/1988 |
| JP | 63-218640 | 9/1988 |
| JP | 63-222139 | 9/1988 |
| JP | 4-164042 | 6/1992 |

OTHER PUBLICATIONS

Boy Cornils, et al., Aqueous–Phase Organometallic Catalysis, pp. 308–310 and 316–317, "Reaction of Olefins", 1998.

*Primary Examiner*—Sreeni Padmanabhan
(74) *Attorney, Agent, or Firm*—Oblon, Spivak, McClelland, Maier & Neustadt, P.C.

(57) ABSTRACT

Aldehydes are prepared by a process, which comprises:

hydroformylating olefins having 3 to 21 carbon atoms under an atmosphere of $CO/H_2$ in the presence of a rhodium catalyst in a hydroformylation reactor; and upon discharging the reaction product from the reactor,
  a) separating the discharged material into a gaseous phase and a liquid phase,
  b) separating the liquid phase into a top fraction containing unconverted olefins and aldehydes and a bottoms fraction containing the rhodium catalyst, and
  c) cooling the bottoms fraction below the temperature of the material discharged from the hydroformylation reactor and feeding a gas containing carbon monoxide into the bottoms fraction.

16 Claims, 3 Drawing Sheets

Stabilization of Catalyst By Synthesis Gas-
Influence of Synthesis Gas Pressure at 120°C

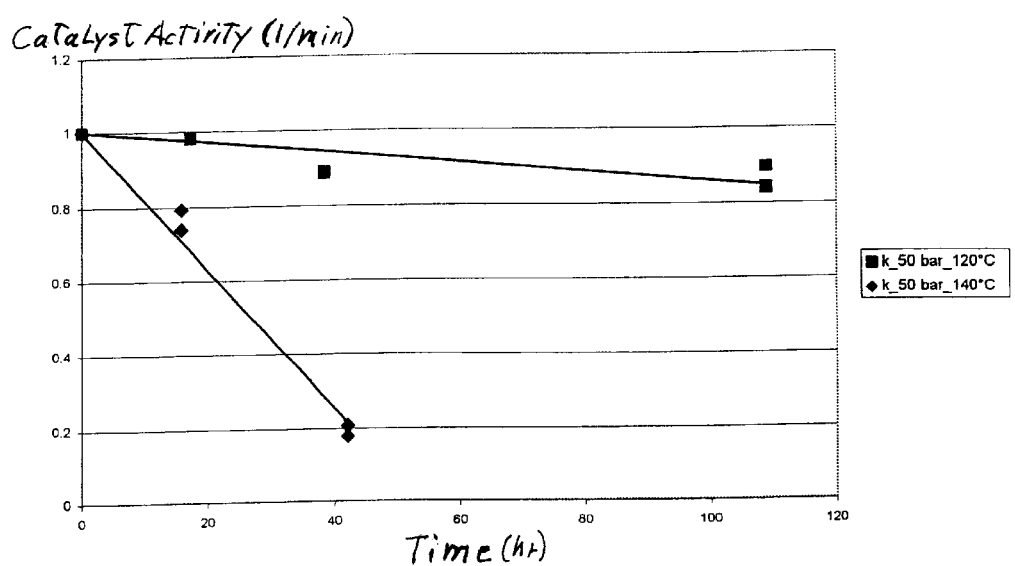
Fig. 3 Stabilization of Catalyst By Synthesis Gas - Influence of Temperature at 50 bar Synthesis Gas Pressure

STABILIZING RHODIUM CATALYSTS FOR THE HYDROFORMYLATION OF OLEFINS

BACKGROUND OF THE INVENTION

1. Field of the Invention

The present invention relates to an improved process for manufacturing aldehydes through hydroformylation of olefins by reducing catalyst deactivation in the regeneration of rhodium catalysts.

2. Description of the Background

On a commercial scale, hydroformylation of olefins is performed with cobalt or with rhodium catalysts. Here, the use of rhodium catalysts is mostly advantageous, as greater selectivity and product yields can be achieved thereby. However, compared to cobalt, rhodium is more expensive; in the hydroformylation of olefins to the corresponding aldehydes with rhodium catalysts the catalyst is a cost factor that is not insignificant. In order to increase economic efficiency, the specific catalyst consumption must be reduced. This factor is understood to be the quantity of catalyst that must be provided to the process during long-term operation in order to guarantee a constant activity level.

The rhodium-catalyzed conversion of olefins to the corresponding aldehydes occurs mostly in the homogenous liquid phase. With the hydroformylation of propene a process has been established in the meantime, wherein the catalyst is present dissolved in a second liquid phase; however, the applicability of this process to longer-chain olefins is limited.

With hydroformylation in the homogenous phase, wherein catalyst, olefins, products, solvents, and the like are present in one phase, the problem which arises is the separation of the catalyst from the products after the reaction is complete. This can be done by distilling the unconverted educt and the products. The catalyst, mostly dissolved in high-boiling constituents in the bottom, is then returned to the reactor. Distillation can be performed either continuously or discontinuously.

In the case of separation by means of distillation, a degree of decomposition or deactivation of the catalyst is often determined. In particular, in the hydroformylation of longer-chain olefins, distillation of the products can only be conducted at increased temperatures and/or reduced pressures because of the boiling points of the products.

Several methods are known for reducing rhodium deactivation during regeneration of the reactor discharge in hydroformylation processes.

EP 0272608 B1 describes a process wherein a rhodium catalyst having triphenylphosphine oxide ligands is utilized for hydroformylation. In the regeneration of the discharge from the reaction, triphenylphosphine (nine-fold quantity relative to rhodium) is added to the discharge prior to its distillation. The distillation residue contains rhodium complexes with triphenylphosphine as ligands, as well as triphenylphosphine and triphenylphosphine oxide. In this mixture the free and complexed triphenylphosphine is oxidized to triphenylphosphine oxide. This catalyst solution is returned to the reactor. Oxygen or a peroxide is utilized to oxidize the triphenylphosphine. Further variants of this method are known and described in JP 63 222 139, JP 63 208 540, DE 3 338 340 and JP 63 218 640.

These processes have the following disadvantages: Triphenylphosphine is consumed constantly. The equivalent quantity of triphenylphosphine oxide is produced by oxidation. In order to limit its concentration in the reactor, a discharge flow system is required by which again rhodium is discharged. An oxidizing apparatus is also necessary. The oxidation process involves costs for the oxidizer unless it is conducted with air.

Other processes using other phosphorus ligands which stabilize the rhodium are described in the relevant literature, such as U.S. Pat. No. 4,400,547.

U.S. Pat. Nos. 5,731,472 and 5,767,321 and EP 0 149 894 describe processes for the hydroformylation of n-butenes. Rhodium catalysts containing phosphite ligands and stabilized by addition of amines are disclosed in these patents. The drawback to the addition of amines is that the amines can act as catalysts for aldol condensation and thus the formation of high boilers is favored.

Hydroformylation of a $C_8$ olefin mixture, manufactured by dimerizing butenes, under the catalysis of rhodium complexes and their stabilization with substituted phenols is described in JP-04-164042. The rhodium compound, ligand and stabilizer are used here in a molar ratio of 1/10/50. The disadvantages of this process are the costs for the stabilizer and the expense of separating it. A need, therefore, continues to exist for a process for the hydroformylation of olefins in which deactivation of the rhodium catalyst is extensively suppressed.

SUMMARY OF THE INVENTION

Accordingly, one object of the present invention is to provide a hydroformylation process in which deactivation of the rhodium catalyst is suppressed.

Briefly, this object and other objects of the present invention as hereinafter will become more readily apparent can be attained by a process for manufacturing aldehydes, which comprises:

hydroformylating an olefin having 3 to 21 carbon atoms under an atmosphere of $CO/H_2$ in the presence of a rhodium catalyst in a hydroformylation reactor;

upon discharging the reaction product from the reactor, a) separating the discharged material into a gaseous phase and a liquid phase, b) separating the liquid phase into a top fraction containing unconverted olefins and aldehydes and a bottoms fraction containing the rhodium catalyst, and c) cooling the bottoms fraction below the temperature of the material discharged from the hydroformylation reactor and feeding a gas containing carbon monoxide into the bottoms fraction.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 is a plot showing rhodium catalyst activity over time (hr) as influenced by temperature at constant synthesis gas pressure.

DETAILED DESCRIPTION OF THE PREFERRED EMBODIMENTS

Figure 1:
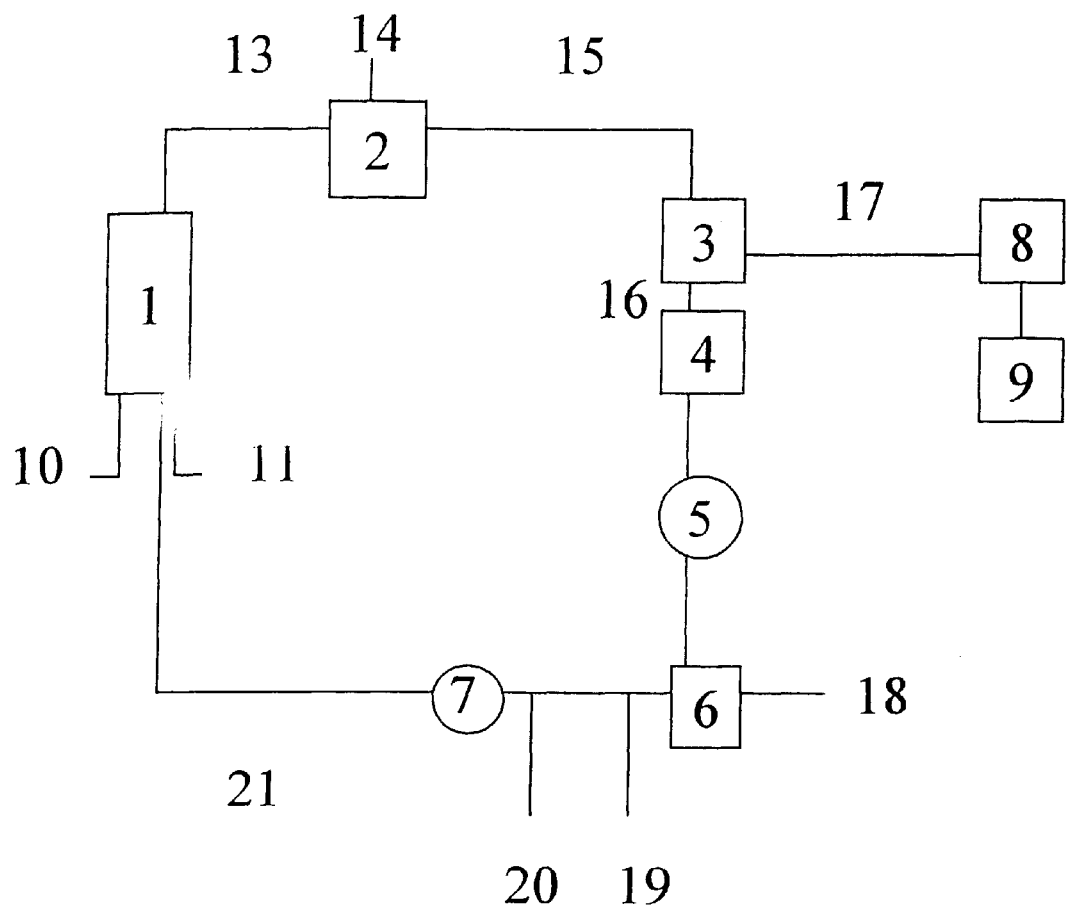
FIG. 1 is a schematic of a hydroformylation plant.

It has been surprisingly discovered that a rhodium catalyst solution stabilized with carbon monoxide is stable in storage for several weeks. Thus, the activity loss of the catalyst during the regeneration of the material discharged from the hydroformylation can be considerably reduced.

An aspect of the present invention is therefore the storage of catalyst solutions containing rhodium, in particular those which are obtained from carbonylation processes, while maintaining their activity. According to the present invention, the activity of a catalyst is maintained when catalyst solutions are stored at a temperature below 90° C., preferably below 60° C., under a carbon monoxide partial pressure of 0.1 to 300 bar, preferably from 5 to 64 bar.

The process of the present invention has the following advantages when compared to known processes: The catalyst is barely deactivated during regeneration. No additional materials, which burden the process by their material costs, are required. The catalyst is stabilized with a substance present in the reactor anyway. It is possible to store the catalyst solution without loss of activity. This is of particular advantage in the case of long periods stoppages, such as for major repairs or inspections, or for batch production.

Hydroformylation is conducted in a homogenous phase in a reactor by known processes as described, for instance by B. Comils, W. A. Herrmann, 'Applied Homogeneous Catalysis with Organometallic Compounds', Vol. 1 & 2, VCH, Weinheim, N.Y., 1996. All olefins having 2 to 20 carbon atoms can be considered as educts, in particular, butenes, pentenes, hexenes and octenes, and in particular dibutene obtained from butene oligomerization. The product flow from the hydroformylation reactor, consisting of aldehydes, alcohols, unconverted olefins, high boilers, catalyst system, by-products and decomposition products, is first separated in a separating stage, process step a) into a gaseous and a liquid phase. The gaseous phase contains the majority of the unconverted synthesis gas and, depending on the temperature and pressure, varying amounts of unconverted olefins, aldehydes, hydrocarbons and other components. The liquid phase, by comparison, predominantly comprises the hydroformylation products and unconverted olefins. The temperature in this separating stage is 30° C. to 180° C., preferably 50° C. to 150° C.. Separation takes place under a carbon monoxide partial pressure of 0.5 to 100 bar, preferably at 1 to 35 bar. These conditions guarantee that the rhodium is stabilized also in this part of the plant. Technically, this separation can take place both at the top of the hydroformylation reactor or in a separate apparatus, such as in a flasher. If the reactor is operated at a higher pressure than the separation stage, pressure is released between these stages. The carbon monoxide partial pressure can be maintained either by the gas mixture introduced into the hydroformylation reactor or by the addition of a gas containing carbon monoxide.

Because the catalyst can react further with unconverted olefins, the risk of catalyst decomposition is increased because of the possible impoverishment of synthesis gas in the liquid phase, consequently, a short dwell time of the liquid phase is desired in this separation stage. Dwell times of less than 30 and preferably less than 15 minutes are beneficial.

After being separated into gas and liquid the liquid phase is fractionated by distillation into a top and bottom fraction (fractionating step, process step b)). The catalyst is accordingly found in the bottom fraction, dissolved in high boilers, which are either added to the process or formed therein. The lower boiling top fraction primarily contains the oxo products and the unconverted olefins.

The average dwell time of the liquid phase in the fractionating step is less than 15 minutes, preferably less than 5 minutes and especially preferably less than 2 minutes. For separating, the fractionating step b) can have a flasher, a falling film evaporator, a thin film evaporator or comparable apparatus, which enable a mild separation. Combinations of these units may also be employed, such as for example a falling film evaporator whose bottom product is transferred to a thin film evaporator.

The pressure in the fractionating step ranges from 0.01 mbar to 1 bar, preferably from 10 mbar to 1 bar. The temperature ranges from 40° C. to 180° C., preferably 80° C. to 150° C. The bottom fraction, which originates from the fractionating step, is promptly cooled down to temperatures of 10° C. to 120° C., preferably to temperatures of 40° C. to 90° C. and under a carbon monoxide partial pressure of 0.1 bar to 300 bar, in particular 5 to 64 bar. Pure carbon monoxide, synthesis gas or other mixtures of carbon monoxide with inert gases such as nitrogen, carbon dioxide, hydrogen and/or methane can be used as a carbon monoxide-containing gas.

One possible configuration of this process stage is to cool the high boiler from the fractionation step in a cooler or alternatively by mixing it with a cooler liquid, preferably with feed olefin, and then to pump it by means of a pump into a vessel containing carbon monoxide, such as for example an agitated tank, a pressure vessel or high-pressure piping.

The catalyst solutions are stored preferably at temperatures that are lower than the outlet temperatures of the catalyst solution from process step b). Preferred storage temperatures of the bottom fraction are therefore 10° C. to 120° C., in particular 40° C. to 90° C.. Optionally, a solvent can be added to the catalyst solution to be stored; appropriately a substance present in the process, such as, for example, educt (olefin), product (aldehyde) or hydrogenated product (alcohol).

This catalyst solution, that is, the bottom fraction of process step b), can be returned wholly or partly to the hydroformylation reactor. The vapors which accumulate in fractionation step b), that is, unconverted olefin and the hydroformylation products, are processed according to known methods.

Having now generally described this invention, a further understanding can be obtained by reference to certain specific Examples which are provided herein for purposes of illustration only and are not intended to be limiting unless otherwise specified.

EXAMPLES

Example 1

Hydroformylation was performed in a technical pilot plant (FIG. 1) as follows: Olefin (10), synthesis gas (11) and catalyst solution (21) are introduced to a bubble column (1) in a volume of 60 liters. The pressure of the hydroformylation discharge material (13) is reduced to 5 bar in a flash chamber (2). The escaping gas (14) is cooled in a cooler, not illustrated, and the accumulating condensate is combined with liquid (15). The liquid phase (15) accumulating in the flash container (2) is separated into a top fraction (17) and a bottom fraction (16) in the thin film evaporator (3). Crude product (17) is condensed in the cooler (8) and collected in container (9). Bottom product (16) containing the catalyst dissolved in high boilers is cooled in cooler (4) (see Table 3) and conveyed to interim tank (6) by means of pump (5). A pressure of 10 bar is adjusted in tank (6) with synthesis gas (18). The temperature of the catalyst solution (16) in tank (6) was determined as shown in Table 3. The catalyst solution (16) is brought to the desired activity in reactor (1) by removing a partial quantity (19) and adding a catalyst precursor (rhodium compound and ligand) (20), and is then returned to the hydroformylation reactor (1) as a solution (21) via pump (7).

Table 1 illustrates typical mass throughput of the educts and catalyst concentrations

| Olefin | di-n-butene | 5 kg/h |
| --- | --- | --- |
| Synthesis gas | CO/H$_2$ (1/1) | 2 kg/h |
| Rhodium compound | rhodium octanoate | (30–90 ppm Rh in reactor 1) |
| Ligand | tris(2,4-di-tert-butylphenyl)-phosphite | (20 mol ligand/mol Rh) |

Table 2 illustrates the test parameters that were maintained during the overall trial.

| Pressure in reactor 1 | 50 bar |
| --- | --- |
| Temperature in reactor 1 | 130° C. |
| Pressure in thin film evaporator 3 | 60 mbar |
| Temperature in thin film evaporator 3 (Outlet temperature at the bottom) | 140° C. |

The activity of the catalyst was monitored by the conversion achieved in the reactor. As soon as the conversion of olefin dropped below 95% a part of the catalyst solution was removed from tank (6) and replaced by fresh catalyst precursor (rhodium salt and ligand), so that the conversion rate returned to over 95%. A small catalyst loss from the high boiler discharge was also replaced.

With different temperatures in the cooler (4) (outlet temperature of catalyst solution), the following quantities of rhodium (calculated as metal) had to be added subsequently in order to maintain the conversion level. (Table 3):

| Cooler 4 temperature | Tank 6 temperature | Rhodium (g), per metric ton of converted olefin |
| --- | --- | --- |
| No cooling | 70° C. to 90° C. | 2.1 |
| 60° C. | 40° C. to 55° C. | 0.9 |

Example 2

Decrease of catalytic activity depending on synthesis gas pressure.

In a 3-liter autoclave (Büchi) 350 g toluene, 3.03 g tris(2,4-di-tert-butylphenyl)phosphite and 0.096 g rhodium octanoate were pretreated under 50 bar synthesis gas pressure (a CO/H$_2$ ratio of 1/1) for one hour at 120° C.. A sample was then taken and the activity of the catalyst was determined in a second autoclave through a hydroformylation reaction with cyclooctene (at 120° C., 50 bar synthesis gas pressure). Next, the catalyst was subjected to thermal stress in the first autoclave over a period of several hours, during which time samples were taken and tested for catalytic activity in a similar manner to which the initial activity was tested. The experiment was repeated at different temperatures and synthesis gas pressures.

Figure 2:
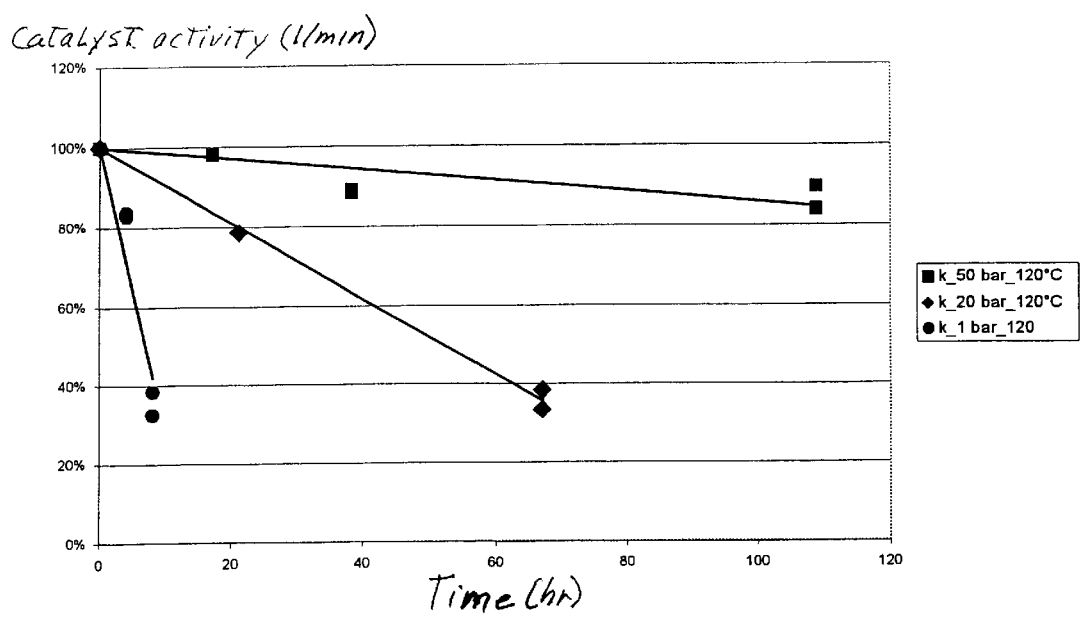
FIG. 2 is a plot showing rhodium catalyst activity over time (hr) as influenced by synthesis gas pressure at constant temperature.

FIG. 2 illustrates the influence of the synthesis gas pressure on the activity and the stability of the catalyst (standardized activity, fresh catalyst has 100% or one unit of activity). At a synthesis gas pressure of 50 bar more than 80% of the initial activity is still present after more than 100 hours, while at 20 bar synthesis gas pressure the activity drops below 40% of the initial activity after just 65 hours. The temperature in all experiments is the same at 120° C..

FIG. 3 illustrates the influence of the temperature on the catalyst stability at a constant synthesis gas pressure of 50 bar. A temperature increase of 120° C. to 140° C. leads to a sharp acceleration in the decomposition of the catalyst.

The disclosure of German priority application Serial Number 10048301.1 filed Sep. 29, 2000 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent is:

1. A process for manufacturing aldehydes, which comprises:
   hydroformylating olefins having 3 to 21 carbon atoms under an atmosphere of CO/H$_2$ in the presence of a rhodium catalyst in a hydroformylation reactor; and
   upon discharging the reaction product from the reactor,
   a) separating the discharged material into a gaseous phase and a liquid phase,
   b) separating the liquid phase into a top fraction containing unconverted olefins and aldehydes and a bottoms fraction containing the rhodium catalyst, and
   c) cooling the bottoms fraction below the temperature of the material discharged from the hydroformylation reactor and feeding a gas containing carbon monoxide into the bottoms fraction.

2. The process as claimed in claim 1, wherein, in the step of the separation of discharged material into a gaseous phase and a liquid phase, the carbon monoxide is adjusted to a partial pressure of 0.5 to 100 bar.

3. The process as claimed in claim 1, wherein the process of separation in step b) is conducted with a falling film evaporator, a thin film evaporator, a flasher or a combination of these units.

4. The process as claimed in claim 1, wherein the average dwell time of the liquid phase in process step b) is less than 15 minutes.

5. The process as claimed in claim 1, wherein the average dwell time of the bottom fraction of process step b) is less than 2 minutes.

6. The process as claimed in claim 1, wherein the temperature in process step b) is 40° C. to 180° C..

7. The process as claimed in claim 6, wherein the temperature in process step b) is 80° C. to 150° C.

8. The process as claimed in claim 1, wherein the pressure in process step b) is 0.01 mbar to 1 bar.

9. The process as claimed in claim 8, wherein the pressure in process step b) is 10 mbar to 1 bar.

10. The process as claimed in claim 1, wherein the bottom fraction of process step c) is under a carbon monoxide partial pressure of 0.1 to 300 bar.

11. The process as claimed in claim 10, wherein said bottom fraction is under a carbon monoxide partial pressure of 5 to 64 bar.

12. The process as claimed in claim 1, wherein the gas containing carbon monoxide is synthesis gas, pure carbon monoxide, or mixtures of carbon monoxide with nitrogen, methane, hydrogen and/or carbon dioxide.

13. The process as claimed in claim 1, wherein the bottom fraction of process step c) is cooled to temperatures of 10° C. to 120° C..

14. The process as claimed in claim 13, wherein the bottom fraction is cooled to temperatures of 40° C. to 90° C..

15. The process as claimed in claim 1, wherein the bottom fraction of process step c) is returned wholly or partly to the hydroformylation reactor.

16. The process as claimed in claim 1, wherein the olefin starting material is dibutene, butenes, pentenes, hexenes or octenes.

* * * * *

UNITED STATES PATENT AND TRADEMARK OFFICE
CERTIFICATE OF CORRECTION

PATENT NO.     : 6,500,991 B2
DATED          : December 31, 2002
INVENTOR(S)    : Wiese et al.

It is certified that error appears in the above-identified patent and that said Letters Patent is hereby corrected as shown below:

<u>Title page,</u>
Item [75], the 3rd and 4th inventors names are spelled incorrectly.
Item [75] should read:

-- [75]  Inventors:  Klaus-Diether Wiese, Haltern (DE); Martin Trocha, Essen (DE); Dirk Röttger, Recklinghausen (DE); Walter Tötsch, Marl (DE); Alfred Kaizik, Marl (DE); Wilfried Büschken, Haltern (DE) --

Signed and Sealed this

Eighth Day of July, 2003

JAMES E. ROGAN
*Director of the United States Patent and Trademark Office*